(12) United States Patent
Hinkel et al.

(10) Patent No.: US 8,805,616 B2
(45) Date of Patent: Aug. 12, 2014

(54) METHOD TO CHARACTERIZE UNDERGROUND FORMATION

(75) Inventors: Jerald J. Hinkel, Houston, TX (US);
Dean Willberg, Tucson, AZ (US);
Markus Pagels, West Jordan, UT (US)

(73) Assignee: Schlumberger Technology Corporation, Sugar Land, TX (US)

( * ) Notice: Subject to any disclaimer, the term of this patent is extended or adjusted under 35 U.S.C. 154(b) by 726 days.

(21) Appl. No.: 12/974,229

(22) Filed: Dec. 21, 2010

(65) Prior Publication Data
US 2012/0152548 A1   Jun. 21, 2012

(51) Int. Cl.
*G01V 9/00*   (2006.01)
*G01N 24/08*   (2006.01)

(52) U.S. Cl.
CPC .................................. *G01N 24/081* (2013.01)
USPC ............................................. 702/11; 702/12

(58) Field of Classification Search
USPC .................. 702/11, 12, 45, 47, 50, 151, 153; 73/38–41
See application file for complete search history.

(56) References Cited

U.S. PATENT DOCUMENTS

| | | | |
|---|---|---|---|
| 3,133,132 A | 5/1964 | Loeb et al. | |
| 3,133,137 A | 5/1964 | Loeb et al. | |
| 3,551,331 A | 12/1970 | Cescon et al. | |
| 3,683,674 A | 8/1972 | Roy | |
| 4,253,327 A | 3/1981 | Wiley | |
| 4,339,948 A | 7/1982 | Hallmark | |
| 4,699,002 A * | 10/1987 | Rockley | 73/152.07 |
| 4,851,394 A | 7/1989 | Kubodera | |
| 5,041,225 A | 8/1991 | Norman | |
| 5,079,948 A | 1/1992 | Collins et al. | |
| 5,086,643 A | 2/1992 | Marek | |
| 5,162,733 A | 11/1992 | Baldwin | |
| 5,265,462 A * | 11/1993 | Blauch et al. | 73/38 |
| 5,411,086 A | 5/1995 | Burcham et al. | |
| 5,425,265 A * | 6/1995 | Jaisinghani | 73/38 |
| 5,563,338 A | 10/1996 | Leturmy et al. | |
| 5,731,511 A * | 3/1998 | Roque et al. | 73/38 |
| 6,021,661 A | 2/2000 | Lowell et al. | |
| 6,069,118 A | 5/2000 | Hinkel et al. | |
| 6,229,312 B1 | 5/2001 | Fleury et al. | |
| 6,370,947 B1 | 4/2002 | Casati et al. | |
| 6,453,727 B1 | 9/2002 | Lenormand et al. | |

(Continued)

FOREIGN PATENT DOCUMENTS

| | | | |
|---|---|---|---|
| WO | 2010083388 A2 | 7/2010 | |
| WO | 2010083388 A3 | 11/2010 | |

OTHER PUBLICATIONS

Jack Dvorkin, Kozeny-Carman Equation Revisited, 2009, pp. 1-16.*

(Continued)

*Primary Examiner* — Michael Nghiem
*Assistant Examiner* — Eman Alkafawi
(74) *Attorney, Agent, or Firm* — Cathy Hewitt

(57) ABSTRACT

A method for determining a characteristic of an underground formation with a fluid is described. The method includes providing a sample material of the underground formation; measuring the permeability and the porosity of the sample material; performing a drainage test on the sample material using the fluid; estimating the threshold pressure of the sample material from the drainage test, the permeability and the porosity measurements; and determining the receding contact angle of the fluid on the sample material from the threshold pressure. The sample material can be disaggregated material.

24 Claims, 3 Drawing Sheets

(56) References Cited

U.S. PATENT DOCUMENTS

| | | | |
|---|---|---|---|
| 6,651,741 | B2 | 11/2003 | Bassin et al. |
| 6,890,373 | B2 * | 5/2005 | Nemoto et al. ............ 95/90 |
| 6,929,069 | B2 | 8/2005 | Hinkel et al. |
| 6,945,327 | B2 | 9/2005 | Ely et al. |
| 7,054,749 | B1 * | 5/2006 | O'Meara, Jr. ............ 702/6 |
| 7,255,166 | B1 * | 8/2007 | Weiss ............ 166/250.02 |
| 7,398,829 | B2 | 7/2008 | Hutchins et al. |
| 7,533,725 | B2 | 5/2009 | Mese et al. |
| 7,549,472 | B2 | 6/2009 | Morrow et al. |
| 7,849,736 | B2 | 12/2010 | Ikeda et al. |
| 8,302,691 | B2 | 11/2012 | Reddy et al. |
| 2002/0029615 | A1 | 3/2002 | Lenormand et al. |
| 2002/0044804 | A1 * | 4/2002 | Kimura et al. ............ 399/325 |
| 2003/0070805 | A1 | 4/2003 | Bassin et al. |
| 2004/0157749 | A1 | 8/2004 | Ely et al. |
| 2004/0255650 | A1 | 12/2004 | Moudgil et al. |
| 2006/0047432 | A1 * | 3/2006 | Egermann et al. ............ 702/12 |
| 2006/0116828 | A1 * | 6/2006 | Chen et al. ............ 702/22 |
| 2008/0046202 | A1 * | 2/2008 | Allende-Blanco et al. ...... 702/50 |
| 2008/0120034 | A1 * | 5/2008 | Georgi et al. ............ 702/6 |
| 2008/0156484 | A1 | 7/2008 | Mese et al. |
| 2008/0159260 | A1 | 7/2008 | Vobbilisetty et al. |
| 2008/0173451 | A1 | 7/2008 | Reddy et al. |
| 2008/0221800 | A1 * | 9/2008 | Gladkikh et al. ............ 702/11 |
| 2008/0236845 | A1 | 10/2008 | Morrow et al. |
| 2009/0159260 | A1 | 6/2009 | Ikeda et al. |
| 2010/0058854 | A1 * | 3/2010 | Waters et al. ............ 73/152.41 |
| 2010/0096128 | A1 | 4/2010 | Hinkel et al. |
| 2010/0096129 | A1 | 4/2010 | Hinkel et al. |
| 2010/0268488 | A1 * | 10/2010 | Bismarck et al. ............ 702/50 |
| 2011/0108271 | A1 | 5/2011 | Hinkel et al. |
| 2012/0151998 | A1 | 6/2012 | Willberg et al. |
| 2012/0152547 | A1 | 6/2012 | Hinkel |
| 2012/0152548 | A1 | 6/2012 | Hinkel et al. |
| 2012/0241149 | A1 * | 9/2012 | Chen et al. ............ 166/250.01 |
| 2013/0152671 | A1 * | 6/2013 | Sinha et al. ............ 73/38 |

OTHER PUBLICATIONS

Abdallah, W. et al, "Fundamentals of Wettability", Oilfield Review, May 2007 Schlumberger Wettability Workshop, Bahrain, Summer 2007, pp. 44-61.

"Recommended Practices for Core Analysis", American Petroleum Institute, Feb. 1998, 236 pages.

Amott, E., "Observations Relating to the Wettability of Porous Rock", SPE 1167-G, 1959, vol. 216, pp. 156-162.

Amyx, J. W. et al, "Petroleum Reservoir Engineering", McGraw-Hill Book Company, New York, NY, 1960, pp. 115.

Aronofsky, J. S. et al, "A Model for the Mechanism of Oil Recovery from the Porous Matrix Due to Water Invasion in Fractured Reservoirs", SPE 932-G, Petroleum Transactions, AIME, vol. 213, 1958, pp. 17-19.

Ayappa, K.G. et al, "Capillary Pressure: Centrifuge Method Revisited", AIChE Journal, 1989, vol. 35, No. 3, pp. 365-372.

Babadagli, T. et al, "Analysis of Counter-Current Gas-Water Capillary Imbibition Transfer at Different Temperatures", Journal of Petroleum Science and Engineering, 55, 2007, pp. 277-293.

Babadagli, T., "Analysis of Oil Recovery by Spontaneous Imbibition of Surfactant Solution", Oil & Gas Science and Technology—Rev. IFP, vol. 60, No. 4, 2005, pp. 697-710.

Behbahani, H. S. et al, "Simulation of Counter-Current Imbibition in Water-Wet Fractured Reservoirs", J. Petroleum Science and Engineering, 50, 2006, pp. 21-39.

Bennion, D. B. et al, "Low Permeability Gas Reservoirs: Problems, Opportunities and Solutions for Drilling, Completion, Stimulation and Production", SPE 35577, Gas Technology Conference, Calgary, Alberta, Canada, Apr. 28-May 1, 1996, pp. 117-131.

Bennion, D. B. et al, "Formation Damage Processes Reducing Productivity of Low Permeability Gas Reservoirs", SPE 60325, 2000 SPE Rocky Mountain Regional/Low Permeability Reservoirs Symposium and Exhibition, Denver, CO, Mar. 12-15, 2000, pp. 1-19.

Bentsen, R. G. et al, "Using Parameter Estimation Techniques to Convert Centrifuge Data Into a Capillary-Pressure Curve", SPEJ, Feb. 1977, pp. 57-64.

Boyer, C. et al, "Producing Gas from Its Source", Oilfield Review, Autumn 2006, pp. 36-49.

Briggs, L. J. et al, "The Moisture Equivalents of Soil", Bull. No. 45, US Dept. of Agriculture, 1907, pp. 5-23.

Carman, P.C., "Fluid Flow Through a Granular Bed", Trans. Inst. Chem. Eng., London, 1937, 15, pp. 150-156.

Carman, P.C., "The Determination of the Specific Surface of Powders", J. Soc. Chem. Ind., 1938, 57, pp. 225-234.

Cosse, R., "Basics of Reservoir Engineering", Gulf Publishing Company, Houston, TX ,1993, p. 180-181.

Dang-Vu, T. et al, "Wettability Determination of Solids Isolated from Oil Sands", Colloids and Surfaces A: Physiochem. Eng. Aspects 337, 2009, pp. 80-90.

Durbin, R. "Osmotic Flow and Water Across Permeable Cellulose Membranes", J. General Physiology, 1960, pp. 315-326.

Firoozabadi, A. et al, "Drainage Performance and Capillary-Pressure Curves With a New Centrifuge", JPT, Jul. 1988, pp. 913-919.

Fischer, H. et al, "Modeling the Effect of Viscosity Ratio on Spontaneous Imbibition", SPE 102641, 2006 SPE Annual Technical Conference & Exhibition held in San Antonio, TX, Sep. 24-27, 2006, pp. 1-20.

Fox, W. H. et al, "The Spreading of Liquids on Low-Energy Surfaces. II. Modified Tetrafluoroethylene Polymers", J. Colloid Science, 7, 1952, pp. 109-121.

Fuerstenau, D. W. et al, "Assessing Oxidation and the Wettability of Coal by a Film Flotation Technique", ACS Division of Fuel Chemistry Preprints, 32(1), 1987, pp. 417-424.

Gregor, H.P. et al, "Synthetic-Membrane Technology", 239, Scientific American, 1978, pp. 112-128.

Gupta, A. et al, "An Improved Model for Laboratory Measurement of Matrix to Fracture Transfer Function Parameters in Immiscible Displacement", SPE 28929, 1994, pp. 383-396.

Handy, L. L., "Determination of Effective Capillary Pressures for Porous Media from Imbibition Data" SPE 1361-G, presented at Joint SPE-AIChE Meeting on May 19-20, 1959, Kansas City, MO, vol. 219, pp. 75-80.

Hassler, G. I. et al, "Measurement of Capillary Pressures in Small Core Samples", Petroleum Technology, Mar. 1945, pp. 114-123.

Hinkel, J. J., "New Environmentally Friendly Surfactant Enhances Well Cleanup", SPE 82214, SPE European Formation Damage Conference, The Hague, May 13-14, 2003, pp. 1-7.

Hiraski, G. et al, "Surface Chemistry of Oil Recovery from Fractured, Oil-Wet Carbonate Formation", SPE 80988, SPE International Sumposium on Oilfield Chemistry held in Houston, TX, USA, Feb. 5-8, 2003, pp. 1-12.

Hoffman, R.N., "A Technique for the Determination of Capillary Pressure Curves Using a Constantly Accelerated Centrifuge", Trans. A.I.M.E, 228, 1963, pp. 227-235.

Jouniaux, L. et al, "Laboratory Measurements Anomalous 0.1-0.5 Hz Streaming Potential Under Geochemical Changes: Implications for Electrotelluric Precursors to Earthquakes", Journal of Geophysical Research, vol. 201, No. B7, Jul. 1997, pp. 15335-15343.

Kovscek, A. R. et al, "Scaling of Counter-Current Imbibition Processes in Low-Permeability Porous Media", Prepared for US Department of Energy, SUPRI TR-121 Report, Dec. 2000, 29 pages.

Kyte, J.R., "A Centrifuge Method to Predict Matrix-Block Recovery in Fractured Reservoirs", Society of Petroleum Engineers Journal, Jun. 1970, pp. 164-170.

Li, K. et al, "Characterization of Spontaneous Water Imbibition into Gas-Saturated Rocks", SPE 62552, 2000 SPE/AAPG Western Regional Meeting held in Long Beach, California, Jun. 19-23, 2000, pp. 1-12.

Luffel, D.L. et al, "Matrix Permeability of Gas Productive Shales", SPE 26633, 65th Annual Technical Conference and Exhibition of the Society of Petroleum Engineers held in Houston, TX, Oct. 3-6, 1993, pp. 261-270.

Luffel, D.L, "Further Discussion of a Technique for the Determination of Capillary Pressure Curves Using a Constantly Accelerated Centrifuge", SPEJ, Jun. 1964, pp. 191-192.

(56) References Cited

OTHER PUBLICATIONS

McCullough, F.W. et al, "Determination of Interstitial-Water Content of Oil and Gas Sand by Laboratory Tests of Core Sample", Drill. & Prod. Prac. API, 1944, pp. 180-188.
MA, S. et al, "Generalized Scaling of Spontaneous Imbibition Data for Strongly Water-Wet Systems", Petroleum Society of CIM, 1995, pp. 95-138.
Mattax C. C. et al, "Imbibition Oil Recovery from Fractured, Water-Drive Reservoir", SPE 187, Jersey Production Research Co., Tulsa, Oklahoma, Jun. 1962, pp. 177-184.
Paktinat, J. et al, "Field Case Studies: Damage Preventions Through Leakoff Control of Fracturing Fluids in Marginal/Low-Pressure Gas Reservoirs", SPE 100417, 2006 SPE Gas Tehnology Sumposium held in Calgary, Alberta, Canada, May 15-17, 2006, pp. 1-11.
Penny, G. S. et al, "Field Study of Completion Fluids to Enhance Gas Production in the Barnett Shale", SPE 100434, 2006 SPE Gas Technology Symposium held in Calgary, Alberta, Canada, May 15-17, 2006, pp. 1-10.
Purcell, W.R., "Capillary Pressures—Their Measurement using Mercury and the Calculation of Permeability herefrom", PetroleumTransactions, AIME, Feb. 1949, pp. 39-48.
Rajan, R.R., "Theoretically Correct Analytical Solution for Calculating Capillary Pressure-Saturation from Centrifuge Experiments", SPWL 27th Annual Logging Symposium held Jun. 9-13, 1986, pp. 1-18.
Raghuraman, B. et al, "Simultaneous Measurement of Capillary Pressure and Resistivity using the Centrifuge", Journal of Colloid and Interface Science, vol. 200, 1998, pp. 188-191.
Rangel-German, E. R. et al, "Water Infiltration in Fractured Systems: Experiments and Analytical Model", SPE 71618, 2001 SPE Annual Technical Conference & Exhibition held in New Orleans, LA, Sep. 30-Oct. 3, 2001, pp. 1-14.
Rickman, R. et al, "A Practical Use of Shale Petrophysics for Stimulation Design Optimization: All Shale Plays Are Not Clones of the Barnett Shale", SPE 115258, 2008 SPE Annual Technical Conference & Exhibition held in Denver, CO, Sep. 21-24, 2008, pp. 1-11.
Schettler, P.D. et al, "Contributions to Total Storage Capacity in Devonian Shales", SPE 23422, 1991 SPE Eastern Regional Meeting held in Lexington, KY, Oct. 22-25, 1991, pp. 77-88.
Schettler, P.D. et al, "Gas Storage and Transport in Devonian Shales", SPE Formation Evaluation, Sep. 1989, pp. 371-376.
Scholz, M. et al, "Revised Capillary Suction Time (CST) Test", Water Conditioning and Purification, Jan. 2006, pp. 46-52.
Skuse, B. et al, "Computation and Interpretation of Capillary Pressure From a Centrifuge", SPE Formation Evaluation, Mar. 1992, pp. 17-24.
Slobod, R.L. et al, "Use of Centrifuge for Determining Connate Water, Residual Oil, and Capillary Pressure Curves of Small Core Samples", Petroleum Transactions, AIME, 1951, vol. 192, pp. 127-134.
Szabo, M.T., "New Methods for Measuring Imbibition Capillary Pressure and Electrical Resistivity Curves by Centrifuge", SPEJ, Jun. 1974, pp. 243-252.
Thomas, L.K. et al, "Threshold Pressure Phenomena in Porous Media", SPE Journal, Jun. 1968, pp. 174-184.
Washburn, E. W., "The Dynamics of Capillary Flow", The Physical Review, vol. XVII, No. 3 ,1921, pp. 273-283.
Wu, Y. et al, "An Experimental Study of Wetting Behavior and Surfactant EOR in Carbonates with Model Compounds", SPE 99612, presented at 2006 SPE/DOE Symposium on Improved Oil Recovery held in Tulsa, OK, Apr. 22-26, 2006, Mar. 2008 SPE Journal, pp. 26-34.
Zellis, M. et al, "Soil Water Content Determination by Karl Fischer Titration", Soil Science Society of America Journal, 1998, vol. 62:(1), pp. 257-262.
Milner, et al., "Imaging Texture and Porosity in Mudstones and Shales: Comparison of Secondary and Ion-Milled Backscatter SEM Methods," SPE 138975, presented at the Canadian Unconventional Resources & International Petroleum Conference held in Calgary, Alberta, Canada, Oct. 19-21, 2010, 10 pages total, Society of Petroleum Engineers.
Bear, J., "Dynamics of Fluids in Porous Media", Dover Publications, Inc.: New York, 1972, pp. 447-451.
Greenkorn, R. A., "Flow Phenomena in Porous Media", Marcel Dekker, Inc.,: New York, 1983, p. 123.
Katsube, T. J., "Shale Permeability and Pore-Structure Evolution Characteristics", Geological Survey of Canada, Current Research 2000(E-15), 11 pages.
Kozeny, J., "Uber kapillare Leitung des Wassers im Boden","On the capillary conduction of water through soil (ascent, infiltration and application to irrigation)", Holder-Pichler-Tempsky, A. G., Commission Publishers for the Academy of Sciences, Vienna, vol. 136, Sections 1 to 10, 1927, pp. 271-306.
Rosen, M.J., "Surfactants and Interfacial Phenomena", Second Edition, John Wiley & Sons: New York, 1989, pp. 246-248.

* cited by examiner

METHOD TO CHARACTERIZE UNDERGROUND FORMATION

CROSS-REFERENCE TO RELATED APPLICATIONS

This application is related to commonly-assigned U.S. patent application Ser. No. 12/914,463, entitled "Enhancing Hydrocarbon Recovery" and is also related to commonly-assigned and simultaneously-filed U.S. patent application Ser. No. 12/974,116 entitled "Wettability Analysis of Disaggregated Material", which is being filed concurrently with the present application and incorporated herein by reference in its entirety.

FIELD

The patent specification is generally related to hydrocarbon recovery from underground formations. More particularly, this patent specification relates to methods to characterize underground formations and the effect of treatments on underground material leading to enhanced hydrocarbon recovery from such underground formations.

BACKGROUND

Recovering hydrocarbons such as oil and gas from high permeability reservoirs is well understood. However, recovery of hydrocarbon resources from low-permeability reservoirs is more difficult and less well understood (See Boyer, C., et al., *Producing Gas from Its Source*. Oilfield Review, 2006. Autumn 2006: p. 36-49.). Consequently, operators have until recently tended to bypass low permeability reservoirs such as shales in favor of more conventional reservoirs such as sandstones and carbonates.

In order to develop methods to efficiently recover gas from an underground reservoir, it is very useful to gain a good understanding of the chemical nature of the formation. For example, a shale reservoir typically includes a matrix of small pores and may also contain naturally occurring fractures/fissures (natural fractures). These natural fractures are most usually randomly occurring on the overall reservoir scale. The natural fractures can be open (have pore volume) under in-situ reservoir conditions or open but filled in with material (have very little or no pore volume) later in geologic time; for example, calcite ($CaCO_3$). These fractures can also be in a closed-state (no pore volume) due to in-situ stress changes over time. Natural fractures in any or all of these states may exist in the same reservoir. For more complete understanding of the occurrence, properties, behavior, etc. of naturally fractured reservoirs in general, one may review the following references: Nelson, Ronald A., *Geologic Analysis of Naturally Fractured Reservoirs* (2nd Edition), Elsevier, and Aguilera, Roberto, *Naturally Fractured Reservoirs*, PennWell Publishing. The permeability of the shale pore matrix is typically quite low, e.g., in the less than one millidarcy range. In a shale gas reservoir, this presents a problem because the pore matrix contains most of the hydrocarbons. Since the low permeability of the pore matrix restricts fluid movement, it would be useful to understand how to prompt mass transfer of hydrocarbons from the pore matrix to the fracture network.

Tight sandstone reservoirs have dominated the hydraulic fracturing market in North America for years, and due to their relatively simple lithology (when compared to gas shales) they have been assumed to be water wet for most stimulation fluid design programs. Most slickwater stimulation treatments were originally formulated for these tight sandstone reservoirs, and to a great extent were adapted "as is" to the gas shale market as it grew. However, due to the wide variation in mineralogy and lithology of kerogen rich shales, the variation in wetting characteristics from reservoir-to-reservoir, and formation-to-formation, has become a major issue. Some reservoirs with high total organic carbon (TOC) values appear to be predominantly if not completely oil-wet. Other shale-like formations, correctly referred to as mudstones or siltstones, appear to be of mixed wettability. Furthermore, any exploitation of the shale reserves requires injection of large quantities of water-based fluids during hydraulic fracturing treatments—and most of this water is not recovered.

Damage to the fracture conductivity and damage to the near-fracture matrix permeability caused by residual water is a major concern. It is hypothesized by many that fracture cleanup and the formation of water blocks in the matrix will be determined by the extent to which the fracturing fluid wets the formation. The extent to which a fluid wets the surfaces of pores will determine how the fluid penetrates the porous medium by imbibition. The extent to which a fluid wets the surface of the fracture face will strongly influence how effectively gas can displace residual water in the fracture network—and may be a key factor in determining the required fracture conductivity. The contact angle is a quantitative thermodynamic measure of the relative wettability of a substrate with respect to two fluids brought into contact with it.

There is a distinct difference between the advancing, the static and the receding contact angles. While the advancing contact angle describes the dynamic contact angle of a fluid invading a surface, the receding contact angle describes the contact angle of a fluid that is displaced from the surface. Generally, the advancing contact angle is associated with imbibition, the process where a wetting fluid spontaneously displaces a non-wetting fluid from a porous medium. For example, Hirasaki, G. and Zhang, D., "Surface Chemistry of Oil Recovery From Fractured, Oil-Wet Carbonate Formation", SPE 80988 (2003) describe capillary pressure and the effects of surface chemistry on imbibition for oil recovery. On the other hand, the receding contact angle is associated with drainage, the process where a wetting fluid is displaced from a porous medium by a non-wetting fluid. So the advancing contact angle describes the interaction between the fluid and the surface when the fluid flows into the rock and the receding contact angle describes the flow of fluid out of the rock. There can be a large hysteresis between the two dynamic contact angles with the static contact angle, describing the angle formed by a static fluid on a surface, lying in-between but not necessarily in the middle.

When the advancing contact angle is known, a prediction can be made as to how fast a fluid will be imbibed into a certain rock matrix or into a microfracture. With this information, the amount of fluid that is imbibed into the rock in a given time can be calculated. The receding contact angle on the other hand can be used to calculate the drainage of a wetting fluid from a rock for a given pressure applied to a non-wetting fluid. It is not only important to know how fast a fluid is imbibed into a rock, it is equally important to know how easily it comes back out. A large amount of water imbibed into the formation during a treatment may not be a problem when it is quickly driven out of the pore space after the treatment is finished. Contrary, a small amount of imbibed fluid can cause severe water blocks if it cannot be retrieved from the rock matrix. The receding contact angle can also be used to determine how quickly a treatment fluid in the fracture network is displaced by hydrocarbons when the well is put on production. A high receding contact angle indicates easy displacement of the treating fluid by the hydrocarbon from the formation. In order to increase the receding contact angle of the treatment fluid on the fracture surface, surface active additives can be used. The effectiveness of an additive can be measured in a drainage test with rock material that was treated with the respective additive.

Knowing the receding contact angle, treatment fluids could be designed that contain optimum amounts of the right additive for a given rock. For example with hydrophilic surfaces that like to be wetted with water, an additive that makes the surface more hydrophobic may be used so water can be easily expelled or is not taken up in the first place.

SUMMARY

According to some embodiments, a method for determining a characteristic of an underground formation with a fluid is provided. A sample material of the underground formation is provided. The permeability and the porosity of the sample material are measured. A drainage test is performed on the sample material using the fluid. The threshold pressure of the sample material is estimated from the drainage test, the permeability and the porosity measurements. The receding contact angle of the fluid on the sample material is determined from the threshold pressure. The sample material is preferably disaggregated sample material. Advantageously, the disaggregation includes a grinding process. Advantageously, the disaggregated sample material is sieved to a specific size range.

According to some embodiments, the disaggregated material is subjected to spinning in a centrifuge prior to the drainage test. In some embodiments, the sample material is a rock core from the underground formation.

Advantageously, some embodiments comprise performing an imbibition test on the sample material prior to the drainage test. The imbibition test preferably includes an estimation of the advancing contact angle on the sample material.

Advantageously, the permeability of the sample material is measured with an inert gas at different pressures. The porosity of the sample material can be determined using the bulk volume and the grain density of the sample material. The fluid can be a treating fluid and the treating fluid comprises a surfactant type and concentration selected to maximize the receding contact angle of the fluid on the sample material.

According to some embodiments, clay-swelling or other ancillary rock-fluid reactions of the sample material are controlled while performing the drainage test.

According to some embodiments, the underground formation is a low-permeability formation with a reservoir matrix permeability of less than 0.1 mD. The underground formation can also be a low-permeability formation that has a reservoir matrix permeability of less than 1 micro Darcy. The underground formation might be a low-permeability formation penetrated by a wellbore. Advantageously, the wettability of the sample material is deduced from the receding contact angle of the fluid on the sample material.

According to some embodiments a characteristic of an underground formation is determined comprising providing a sample material of the underground formation; determining the threshold pressure of the sample material from a drainage test; computing the average saturation of the sample material using a measured irreducible saturation and the saturation at the threshold pressure; determining the average threshold pressure of the sample material from the average saturation and determining the threshold pressure at the irreducible saturation of the underground formation from the average threshold pressure, the average saturation and the measured irreducible saturation.

According to some embodiments a method for enhancing hydrocarbon recovery from a low-permeability formation is provided. A treating fluid is caused to contact the underground formation such that the treating fluid is imbibed by the formation, thereby increasing hydrocarbon recovery, wherein the treating fluid is selected based at least in part on the determination of the receding contact angle of the treating fluid on the underground formation.

According to some embodiments a formation treating fluid for enhancing hydrocarbon recovery from an underground formation is provided. The formation treating fluid comprises at least one constituent selected based at least in part on a quantitative determination of the permeability and the porosity of the underground formation and a drainage test carried out on the sample of the underground formation and the at least one constituent. Preferably, the drainage test comprises determination of the receding contact angle of the at least one constituent on the sample of the underground formation.

According to some embodiments it is provided a method for determining the effect of a fluid on a rock formation comprising determining the permeability and the porosity of the rock formation; saturating the rock formation with the fluid; determining the threshold pressure of the rock formation imbibed with the fluid from a drainage test, the permeability and the porosity of the rock formation; determining a cleanup ratio of the fluid for the rock formation using the ratio of the threshold pressure and the maximum threshold pressure wherein the maximum threshold pressure is the threshold pressure for a perfectly wetting fluid; determining the effect of the fluid on the rock formation from the cleanup ratio. Advantageously, the receding contact angle of the fluid on the rock formation is determined from the threshold pressure. Advantageously, an imbibition test is performed on the rock formation prior to the drainage test and the imbibition test can include an estimation of the advance contact angle on the rock formation. Advantageously, the effects of a first and second fluids on the rock formation can be compared using the clean-up ratio of the first and second fluids respectively. Advantageously, the rock formation is disaggregated to form a disaggregated rock formation sample and the effect of a fluid on a rock formation are determined from the disaggregated rock formation sample.

According to some embodiments, it is provided a method of selecting an appropriate treatment fluid for enhancing hydrocarbon recovery from an underground formation. The porosity of a first sample material of the underground formation is determined. The first sample material is tested for drainage characteristics for a first candidate fluid. The determination of porosity and testing drainage characteristics is repeated for each of one or more subsequent sample materials from underground formation and each of one or more subsequent candidate fluids. A candidate fluid is selected based at least in part on the drainage testing and porosity determinations, the selected candidate fluid forming at least part of the treatment fluid. Advantageously, each testing for drainage characteristics includes an estimation of the receding contact angle for each sample material and candidate fluid, each estimation of receding contact angle being based in part on the determination of porosity of the sample material, and step of selecting a candidate fluid being based in part on the estimations of receding contact angle. Advantageously, the sample material comprises disaggregated material from the underground formation. Advantageously, the candidate fluid is imbibed in the sample material to reach complete saturation. Advantageously, an imbibition test on the sample material is performed prior to the drainage test and the candidate fluid is selected based at least in part on the fact that, with the candidate fluid, the reduction of the drainage contact angle on the sample material is less than the reduction of the advancing contact angle on the sample material.

According to some embodiments, it is provided a method for determining a characteristic of an underground formation with a fluid comprising providing a sample material of the underground formation; imbibing the sample material with a first imbibing fluid; performing a drainage test on the sample material imbibed with the first imbibing fluid; measuring a surface property of the sample material; repeating steps (b) to (d) for at least a second imbibing fluid; plotting the measured surface properties of the sample material against each surface tension of the first and second imbibing fluids; comparing the resulting curve with a set of curves determined for a material with known wettability; determining the wettability of the sample material from the comparison.

As used herein the term "shale" refers to mudstones, siltstones, limey mudstones, and/or any fine grain reservoir where the matrix permeability is in the nanodarcy to microdarcy range.

As used herein the term "gas" means a collection of primarily hydrocarbon molecules without a definite shape or volume that are in more or less random motion, have relatively low density and viscosity, will expand and contract greatly with changes in temperature or pressure, and will diffuse readily, spreading apart in order to homogeneously distribute itself throughout any container.

As used herein the term "oil" means any naturally occurring, flammable or combustible liquid found in rock formations, typically consisting of mixture of hydrocarbons of various molecular weights plus other organic compounds such as is defined as any hydrocarbon, including for example petroleum, gas, kerogen, paraffins, asphaltenes, and condensate.

As used herein the term "condensate" means a low-density mixture of primarily hydrocarbon liquids that are present as gaseous components in raw natural gas and condense out of the raw gas when the temperature is reduced to below the hydrocarbon dew point temperature of the raw gas.

BRIEF DESCRIPTION OF THE FIGURES

The present disclosure is further described in the detailed description which follows, in reference to the noted plurality of drawings by way of non-limiting examples of exemplary embodiments, in which like reference numerals represent similar parts throughout the several views of the drawings, and wherein.

DETAILED DESCRIPTION

The following description provides exemplary embodiments only, and is not intended to limit the scope, applicability, or configuration of the disclosure. Rather, the following description of the exemplary embodiments will provide those skilled in the art with an enabling description for implementing one or more exemplary embodiments. It being understood that various changes may be made in the function and arrangement of elements without departing from the spirit and scope of the invention as set forth in the appended claims.

Specific details are given in the following description to provide a thorough understanding of the embodiments. However, it will be understood by one of ordinary skill in the art that the embodiments may be practiced without these specific details. For example, systems, processes, and other elements in the invention may be shown as components in block diagram form in order not to obscure the embodiments in unnecessary detail. In other instances, well-known processes, structures, and techniques may be shown without unnecessary detail in order to avoid obscuring the embodiments. Further, like reference numbers and designations in the various drawings indicated like elements.

Also, it is noted that individual embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process may be terminated when its operations are completed, but could have additional steps not discussed or included in a figure. Furthermore, not all operations in any particularly described process may occur in all embodiments. A process may correspond to a method, a function, a procedure, a subroutine, a subprogram, etc. When a process corresponds to a function, its termination corresponds to a return of the function to the calling function or the main function.

Furthermore, embodiments of the invention may be implemented, at least in part, either manually or automatically. Manual or automatic implementations may be executed, or at least assisted, through the use of machines, hardware, software, firmware, middleware, microcode, hardware description languages, or any combination thereof. When implemented in software, firmware, middleware or microcode, the program code or code segments to perform the necessary tasks may be stored in a machine readable medium. A processor(s) may perform the necessary tasks.

Figure 1:
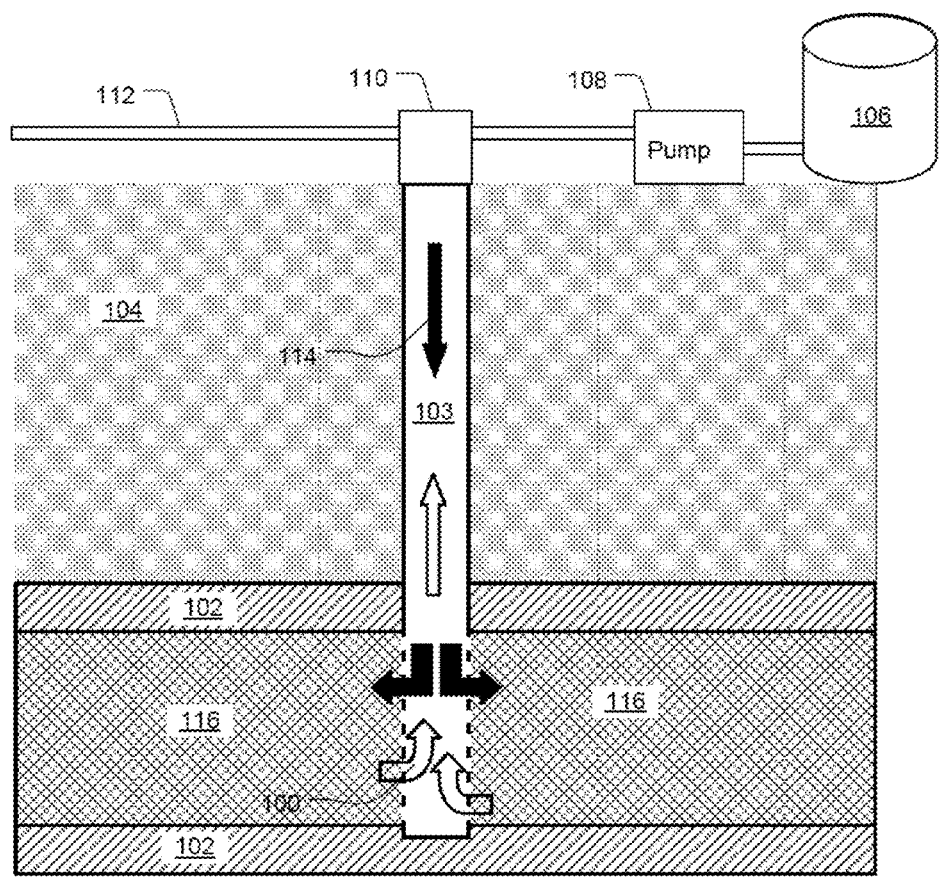
FIG. 1 illustrates a system for enhancing recovery of hydrocarbons from a low-permeability hydrocarbon reservoir, according to some embodiments.

FIG. 1 illustrates a system for enhancing recovery of hydrocarbons (in this example gas 100) from a hydrocarbon reservoir 102, according to some embodiments. The system utilizes a borehole 103 which is formed by drilling through various layers of rock (collectively, overburden 104), if any, to the reservoir 102. The reservoir 102 is described in one example as a shale reservoir. However, according to some embodiments other types of reservoirs can benefit. For example, according to some embodiments the reservoir 102 is another type of reservoir having low permeability or even a conventional type of reservoir. It is also believed that many of the techniques described herein can practically be applied to any reservoirs, including those having low matrix permeability (i.e. between 10 nanodarcies (nD) and 100 mD, where 1 D=9.87×10$^{-13}$ m$^2$). According to some embodiments, the reservoir 102 is heterogeneous and/or has mixed wet characteristics.

The recovery enhancing system of FIG. 1 includes a fluid storage tank 106, a pump 108, a well head 110, and a gas recovery flowline 112. The fluid tank 106 contains a treating fluid formulated to promote imbibition in the low permeability reservoir 102. For example, the treating fluid may be an aqueous solution including surfactants that result in a surface tension adjusted to optimize imbibition based at least in part on determination or indication of the wettability of the formation, permeability of the formation, or both. The treating fluid 114 is transferred from the tank to the borehole using the pump 108, where the treating fluid comes into contact with the reservoir. The physical characteristics of the treating fluid facilitate migration of the treating fluid into the reservoir. In particular, the treating fluid enters the pore space when exposed to the reservoir, e.g., for hours, days, weeks, or longer. Entrance of the treating fluid into the pore space tends to displace gas from the pore space. The displaced gas migrates from a portion of the reservoir 116 to the borehole 103 through the pore space, via the network of natural and/or induced fractures. Within the borehole, the gas moves toward the surface as a result of differential pressure (lower at the surface and higher at the reservoir) and by having a lower density than the treating fluid. The gas is then recovered via the pipe (flowline) at the wellhead. The recovered gas is then transferred directly off site, e.g., via flowline 112.

The receding contact angle can be used to calculate the drainage of a wetting fluid from a rock for a given pressure applied to a non-wetting fluid. The receding contact angle can also be used to determine how quickly a treatment fluid in the fracture network is displaced by hydrocarbons when the well is put on production. A high receding contact angle indicates easy displacement of the treating fluid by the hydrocarbon from the formation. In order to increase the receding contact angle of the treatment fluid on the fracture surface, surface active additives can be used. The effectiveness of an additive can be measured in a drainage test with rock material that was treated with the respective additive.

On the basis of this dynamic contact angle, formation treatments can be optimized so that treatment fluids that contain optimum amounts of the right additive for a given rock are chosen. For example with hydrophilic surfaces that like to be wetted with water, an additive that makes the surface more hydrophobic may be used so water can be easily expelled or is not taken up in the first place. Here, we present an experimental drainage method to measure the saturation dependent capillary pressure in a rock sample with which a receding contact angle of a fluid on a reservoir material can be estimated.

In order to measure a receding contact angle in a sample, the fluid needs to "recede" from the sample. This can be achieved by displacing the fluid with which the sample is saturated with another, immiscible fluid (or gas) that is pressed into the sample. The method most often used in a current practice is a displacement test where a treating fluid, usually gas, is pressed through a rock material of considerable size (about 500 g material). The pressure which is needed to press the liquid through the rock material is recorded. However, viscous fingering and phase trapping can lead to erroneous measurement results. It might also be difficult to calculate a receding contact angle via this method. However, this method can be used as an "index test"—it allows the investigator to compare the relative effects of two fluids on the same rock, but it does not provide satisfactory quantitative fundamental data that can be fed into a mathematical model of the system, for example.

Another method to drive a fluid out of a sample is to place the sample into a centrifuge. At a high enough rotational speed the fluid will flow out of the sample and is replaced—rather than displaced—by either air or another liquid on top of the sample. This way viscous fingering and phase trapping are minimized and it has been found that the required amount of sample can be reduced considerably. McCollough et al (See McCullough, F. W., F. W. Albaugh, and P. H. Jones, Determination of Interstitial-Water Content of Oil and Gas Sand by Laboratory Tests of Core Samples. Drill. & Prod. Prac. API, 1944: p. 180-188) published first centrifuge experiments on sandstone core samples in the petroleum literature in 1944 following the work of earlier soil scientists (1907) (Briggs, L. J. and J. W. McLane, *The Moisture Equivalents of Soil*. Bull. No. 45, US Dept. of Agriculture, 1907: p. 5-23). They determined the saturation of the sample by measuring the electrical conductivity.

Just one year later, in 1945, Hassler and Brunner presented a first mathematical model, which—with refinements—is still widely used in the petroleum industry today (Hassler, G. L. and E. Brunner, Measurement of Capillary Pressures in Small Core Samples. Petroleum Technology, 1945. March 1945: p. 114-123.). They presented a simple approximation to convert average saturation to end-face saturation (Skuse, B., A. Firoozabadi, and H. J. Ramey. Jr., Computation and Interpretation of Capillary Pressure From a Centrifuge. SPE Formation Evaluation, 1992. March 1992: p. 17-24). Comparison with results found by porous-plate method showed good agreement of the drainage capillary pressure curves (Slobod, R. L., A. Chambers, and W. L. J. Prehn, Use of Centrifuge for Determining Connate Water, Residual Oil and Capillary Pressure Curves of Small Core Samples. Trans. A.I.M.E, 1951. 192: p. 127-13). Many variations and improvements to Hassler and Brunner's method of calculating saturation and experimental procedure followed in the next decades (See Hoffman, R. N., *A Technique for the Determination of Capillary Pressure Curves Using a Constantly Accelerated Centrifuge*. Trans. A.I.M.E, 1963. 228: p. 227-235 or Luffel, D. L., *Further Discussion of a Technique for the Determination of Capillary Pressure Curves Using a Constantly Accelerated Centrifuge*. SPEJ, 1964. June 1964: p. 191-192 or Szabo, M. T., *New Methods for Measuring Imbibition Capillary Pressure and Electrical Resistivity Curves by Centrifuges*. SPEJ, 1974. June 1974: p. 243-252 or Firoozabadi, A., H. Soroosh, and G. H. Hasanpour, *Drainage Performance and Capillary-Pressure Curves With a New Centrifuge*. JPT, 1988. July 1988: p. 913-919 and Bentsen, R. G. and J. Anli, *Using Parameter Estimation Techniques To Convert Centrifuge Data Into a Capillary-Pressure Curve*. SPEJ, 1977. February 1977: p. 57-64). In 1986 Rajan proposed an analytical solution to the problem of accounting for the changing centrifugal force along the sample length (see Rajan, R. R., *Theoretically Correct Analytical Solution for Calculating Capillary Pressure-Saturation from Centrifuge Experiments*. SPWL Logging Symp., 1986). This solution, while computationally complex, gives an accurate saturation distribution along the length of the sample and allows converting average saturation into inlet-face saturation.

In equilibrium the capillary pressure in a drainage experiment is equal to the average fluid pressure in a sample in the centrifuge. If the fluid pressure is higher than the capillary pressure, fluid will flow out of the sample. If the fluid pressure is equal or lower than the capillary pressure, the fluid will remain in the sample. The centrifugal pressure, equivalent to a hydrostatic pressure, is given by:

$$p = \rho g h \qquad \text{Eqn. (1)}$$

with $\rho$ being the density of the fluid, g being the acceleration and h being the rock material height. Acceleration is proportional to the distance from the pivot-point of the centrifuge arm and will change along the length of the sample rock material (see Kyte, J. R., *A Centrifuge Method To Predict Matrix-Block Recovery in Fractured Reservoirs*. Society of Petroleum Engineers Journal, 1970. June: p. 164-170). The mean acceleration within the sample and the sample height are given as:

$$\bar{g} = \frac{1}{2}\omega^2(r_1 + r_2) \qquad \text{Eqn. (2)}$$

$$h = r_2 - r_1 \qquad \text{Eqn. (3)}$$

wherein $r_1$ and $r_2$ are the radii of rotation to the inner and the outer faces of the sample, respectively and $\omega$ is the rotation speed of the centrifuge.

Combining equations (1), (2) & (3) leads to an expression for the capillary pressure in a centrifugal drainage experiment:

$$p_c = \frac{1}{2}\rho\omega^2(r_2^2 - r_1^2) \qquad \text{Eqn. (4)}$$

Since $r_2$ is fixed (see FIG. 2), the height L of the sample determines $r_1$. In fact Eqn. (4) should contain the difference of the densities of the wetting and non-wetting fluids $\Delta\rho$. The non-wetting fluid is air, whose density ($\rho=0.0012$ g/cm$^3$) is so small compared to the density of water ($\rho=1$ g/cm$^3$) that we can rightfully neglect it.

At a given angular velocity, a pressure gradient develops in the wetting fluid; the pressure drives the removal of wetting fluid from all capillaries capable of flow at or below that pressure. By increasing the rotational speed, the centrifugal pressure is increased and water is driven out of the sample until the centrifugal pressure equals the capillary pressure. As the pressure is increased, smaller and smaller capillaries will be drained. Since the non-wetting fluid, air in this case, replaces rather than displaces the imbibant, issues of viscous fingering are avoided. The mass m of the removed imbibant is determined after each velocity stage which is held for approximately 10 minutes to ensure equilibrium is reached. The initial mass $m_f$ of imbibant (index f for fluid) is known from the imbibition experiment—it is the difference of the mass of the sample tube before and after the imbibition: $m_f = m_{total} - m_{dry}$. The water driven out of the sample by the centrifugal pressure reduces the average saturation of the sample and the average saturation across the sample can be computed:

$$\bar{S}_w = \frac{m_f - m}{m_f} \qquad \text{Eqn. (5)}$$

The saturation-dependent capillary pressure $p_c$ of the sample is given as:

$$p_c(S_w) = \frac{1}{2}\Delta\rho\omega^2(r_2^2 - r_1^2) \qquad \text{Eqn. (6)}$$

where $\Delta\rho$ is the difference between the gravities of the wetting and non-wetting fluids, $\omega$ is the angular velocity of the centrifuge and $r_1$ and $r_2$ are the radii of rotation to the inner and the outer faces of the sample, respectively. In our measurements the rock sample is saturated with an aqueous fluid that is replaced by air as a non-wetting fluid during the drainage process. The pressure in the non-wetting air is the ambient pressure. The pressure in the wetting phase is actually negative. The method is based upon the reasonable assumption that the outer end of the rock sample remains completely saturated, and the capillary pressure there is zero.

Hassler and Brunner suggest a simple first order correction of the calculated saturation for the fact that the centrifugal acceleration is not the same across the sample (Hassler, G. L. and E. Brunner, *Measurement of Capillary Pressures in Small Core Samples*. Petroleum Technology, 1945. March 1945: p. 114-123).

$$S_w(P_c) = \bar{S}_w + P_c \frac{d\bar{S}_w}{dP_c} \qquad \text{Eqn. (7)}$$

The acceleration depends on the distance of the sample from the axis of rotation in the centrifuge. As the real sample has a definite length the acceleration at the top of the sample is different from that at the bottom of the sample. Given the fact that 65 years ago Hassler and Brunner had to hand-calculate the corrections they argued that for ratios of $r_1/r_2 > 0.7$ a correction would not be necessary. In an experimental setup this would allow uncorrected measurements for sample lengths of up to 5 cm. However, using modern computer technology it is preferable to make the correction for smaller samples also. Our rock sample heights are usually around 3 cm.

If the diameter of the rock sample is small, one can safely ignore radial differences in capillary pressure that occur. The radial change in the gravitational force can also be safely ignored. If the sample is short, relative to the radius of the centrifuge arm, then one can neglect the variation in centrifugal force along the axis of the specimen.

Rajan (Rajan, R. R., *Theoretically Correct Analytical Solution for Calculating Capillary Pressure-Saturation from Centrifuge Experiments*. SPWL Logging Symp., 1986) chose not to ignore the axial variation in capillary pressure, and suggested the following equation to calculate the capillary pressure dependent saturation:

$$S_w(P_{ci}) = \bar{S}_w(P_{ci}) + \frac{2R}{1+R}P_{ci}\frac{d\bar{S}_w(P_{ci})}{dP_{ci}} + \qquad \text{Eqn. (8)}$$

$$\frac{R}{1-R^2}\int_0^{P_{cri}}\left\{\frac{1 - \left[1 - \frac{P_c}{P_{ci}}(1-R^2)\right]^{\frac{1}{2}}}{\left[1 - \frac{P_c}{P_{ci}}(1-R^2)\right]^{\frac{1}{2}}}\right\}^2 \frac{d\bar{S}_w(P_c)}{dP_c}dP_c$$

Figure 2:
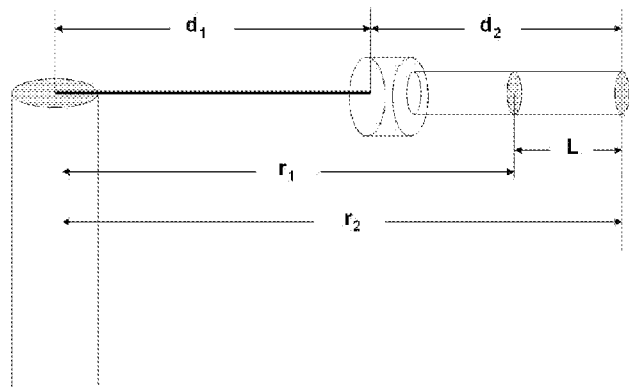
FIG. 2 represents a schematic showing of the spatial relationships during centrifuge test; sample length is L(cm)

In Eqn. 8, $$R = \frac{r_1}{r_2},$$

and $r_1$ and $r_2$ represent the distances of the inlet and outlet faces of the sample from the axis of rotation—see FIG. 2. By eliminating the third term in Eqn. 8 and setting R to 1, the equation proposed by Hassler and Brunner is obtained; therefore, the Rajan method may be seen as a correction to the Hassler and Brunner method.

The main criticism of the Hassler and Brunner and Rajan methods is the need to compute derivatives using the raw data and the potentially large errors that might result. In an embodiment of the invention, a spreadsheet and straightforward numerical techniques were used to analyze data based upon Eqn. 8, and it shows that, when R=0.85, the Rajan method reproduced a theoretical capillary pressure curve with an average error of slightly less than −2% compared to an error obtained using the Hassler and Brunner method of −13.8%.

Ayappa et al. compared three centrifuge data analysis methods and concluded that the Rajan method was the best, especially at lower R values (See Ayappa, K. G. and H. T. Davies, *Capillary Pressure: Centrifuge Method Revisited*. AIChE Journal, 1989. 35(3): p. 365-372).

The threshold pressure is, strictly speaking, the lowest pressure required to force a non-wetting fluid into a porous medium that has been completely saturated with a wetting fluid. If the porous medium is considered to be an ensemble of capillaries of varying radii, then the threshold pressure corresponds to the pressure required to displace wetting fluid from the largest capillaries. Once the largest capillaries have been drained, the displacement pressure must be increased before the next largest capillaries begin to drain, and this process can be continued until no further increase in pressure will remove additional wetting fluid; the saturation at this point is the irreducible saturation.

Estimating the Receding Contact Angle

Bear (see Bear, J., *Dynamics of Fluids in Porous Media*. 1972, New York: Dover Publications, Inc) states that the threshold pressure expression for a capillary can be adapted to a porous medium if the capillary tube radius is replaced by some mean or equivalent diameter r*.

$$P_t = \frac{2\gamma\cos\theta}{r^*} \quad \text{Eqn. (9)}$$

Note that in the equation above the argument presented by Bear has been made more general by not assuming perfect wetting. Based upon a model used to describe imbibition like the one described in U.S. patent application Ser. No. 12/914,463, entitled "Enhancing Hydrocarbon Recovery", the equivalent diameter can be expressed as $$r^* = \sqrt{\frac{8k}{\phi^3}} \quad \text{Eqn. (10)}$$

Making the substitution:

$$P_t = 2\gamma\cos\theta\sqrt{\frac{\phi^3}{8k}} \quad \text{Eqn. (11)}$$

The equation above is correct for terms expressed in SI units. With permeability expressed in mD and expressing the pressure in psi, Eqn. 11 takes the following form $$P_t = 4.616\left(2\gamma\cos\theta\sqrt{\frac{\phi^3}{8k}}\right) = 3.264\gamma\cos\theta\sqrt{\frac{\phi^3}{k}} \quad \text{Eqn. (12)}$$

The question of threshold pressure was investigated by Thomas, Katz and Tek (Thomas, L. K., D. L. Katz, and M. R. Tek, *Threshold Pressure Phenomena in Porous Media*. SPE Journal, 1968. June 1968: p. 174-184). The authors were interested in determining how much overpressure could be used in a natural gas storage system. They were able to show that the threshold pressure could be correlated, across a broad permeability range, using a simple model. Their model relates the threshold pressure to permeability, porosity, surface tension and the formation factor. Thomas et al. derived the following expression:

$$P_t = \frac{0.1461\sigma}{\sqrt{k_0}\,F}\sqrt{\frac{1}{\phi k_D}} \quad \text{Eqn. (13)}$$

Like Bear, the authors assumed that their samples were perfectly wetted by water, i.e. contact angle of 0°. In the equation above, σ is the surface tension, $k_0$ is a shape factor (varies from 2 to 3), $k_D$ is the permeability in Darcy and F is the formation factor.

Through the use of resistivity measurements, it has been determined that rock samples used in applications of the method of the invention were appropriately represented using a formation factor equal to the reciprocal of the square of the porosity (Amyx, J. W., Bass, D. M., and Whiting, R. L., *Petroleum Reservoir Engineering*, McGraw-Hill Book Company, New York, N.Y. (1960) p. 115). Substituting and converting the permeability from Darcys to mD, we obtain:

$$P_t = \frac{0.1461\sigma}{\sqrt{k_0}\,\frac{1}{\phi^2}}\sqrt{\frac{1}{\phi k_D}} = \frac{0.1461\sigma}{\sqrt{k_0}}\sqrt{\frac{\phi^3}{k_D}} = \frac{4.620\sigma}{\sqrt{k_0}}\sqrt{\frac{\phi^3}{k}} \quad \text{Eqn. (14)}$$

Comparing Eqn. 12 with Eqn. 14, we can determine the value of $k_0$ required to make the two approaches equivalent when θ is 0°:

$$3.264\gamma\cos\theta\sqrt{\frac{\phi^3}{k}} = 3.264\gamma\sqrt{\frac{\phi^3}{k}} = \frac{4.620\gamma}{\sqrt{k_0}}\sqrt{\frac{\phi^3}{k}} \quad \text{Eqn. (15)}$$

Solving for $k_0$ yields a value of 2.01, this is within the range specified by Thomas et al. It appears that the model of a porous medium developed to describe imbibition into sample columns is consistent with the model proposed by Thomas et al.

Solving Eqn. 12 for the contact angle, we obtain:

$$\theta = \arccos\left(\frac{P_t}{3.264\gamma}\sqrt{\frac{k}{\phi^3}}\right) \quad \text{Eqn. (16)}$$

The equation above is correct when the threshold pressure is in psi, the permeability is expressed in mD and the surface tension is expressed in dyne/cm.

Estimating the Average Threshold Pressure

The threshold pressure is, strictly speaking, the lowest pressure required to force a non-wetting fluid into a porous medium that has been completely saturated with a wetting fluid. If the porous medium is considered to be an ensemble of capillaries of varying radii, then the threshold pressure corresponds to the pressure required to displace wetting fluid from the largest capillaries. Once the largest capillaries have been drained, the displacement pressure must be increased before the next largest capillaries begin to drain, and this process can be continued until no further increase in pressure will remove additional wetting fluid; the saturation at this point is the irreducible saturation.

The permeability value measured in the laboratory represents an average of the flow through pores of varying sizes. The bundle of capillaries model relates the permeability to the square of the mean capillary radius and the porosity.

We studied synthetic porous media consisting of bundles of capillaries whose radii were geometrically and log-normally distributed. We concluded that the geometric mean provided a good estimate for the mean capillary radius for either geometrically or log-normally distributed radii. Since the capillary pressure varies inversely with radius, the mean capillary pressure will be inversely proportional to the geometric mean of the smallest and largest radii making up the ensemble. Therefore, we used the geometric mean, $P_{pro}$, to compute the receding contact angle using the permeability measured in the laboratory according to $$\cos\theta_A = \frac{P_{pro}\sqrt{k_A}}{3.264\gamma_A\sqrt{\phi_A^3}} \quad \text{Eqn. (17)}$$

From this it can now be given steps to determine the receding contact angle of the concerned rock material.

Figure 3:
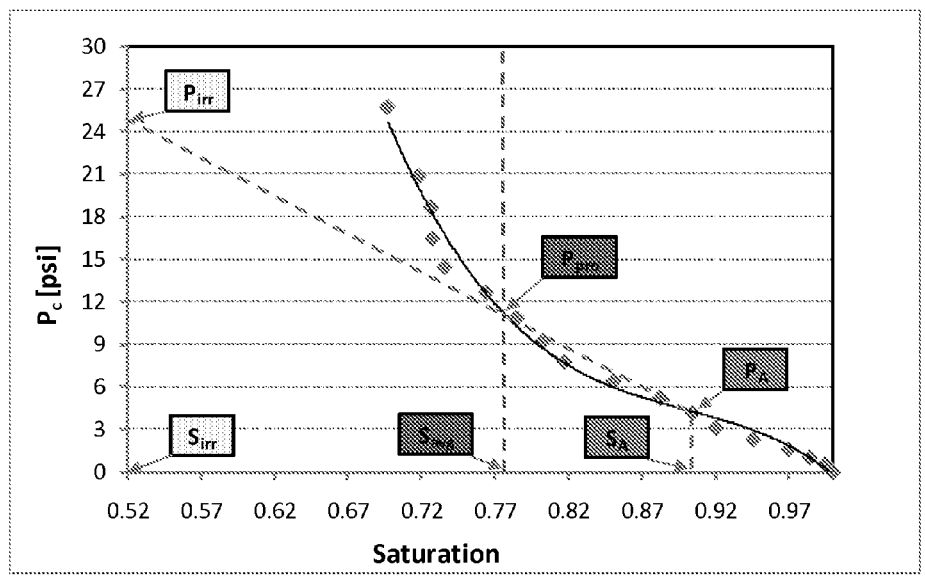
FIG. 3 represents results from a typical drainage test showing how variables are related.

Step 1. Estimate the threshold pressure, $P_A$, (Refer to FIG. 3 for a depiction of the various parameters) from the results of a centrifuge test. The capillary pressure data for the RPM range below 1000 is fitted with a cubic polynomial function and standard mathematical techniques are used to calculate the inflection point which represents the threshold pressure. $P_A$ is directly related to the largest capillary in the ensemble (See Greenkorn, R. A., *Flow Phenomena in Porous Media*. 1983, New York: Marcel Dekker, Inc.).

Step 2. Compute the average saturation ($S_{avg}$) using the measured irreducible saturation ($S_{irr}$) and the saturation at the threshold pressure ($S_A$):

$$S_{avg} = \left[\frac{S_A - S_{irr}}{2}\right] + S_{irr} \quad \text{Eqn. (18)}$$

Step 3. Draw a vertical line (red dashed line in FIG. 3) at $x=S_{avg}$. Note where the vertical line passes through the curve used to fit the data, i.e. the point ($S_{avg}$, $P_{avg}$).

Step 4. Connect the points ($S_A$, $P_A$) and ($S_{avg}$, $P_{avg}$) and extrapolate the line to intersect with the vertical line that passes through the irreducible saturation. The point of intersection is ($S_{irr}$, $P_{irr}$). $P_{irr}$ is associated with the radius of the smallest capillary in the ensemble.

Step 5. The average capillary pressure lies between $P_A$ and $P_{irr}$. Earlier, we concluded that the geometric mean provides a good estimate for the average for either geometrically or log-normally distributed pore sizes, therefore we use the geometric mean, or $$P_{pro} = \sqrt{P_A P_{irr}} \quad \text{Eqn. (19)}$$

Comparing the Effects of Fluid Additives on Porous Materials—Cleanup Ratio

First, a test solution containing additive A in the baseline fluid is imbibed into the porous medium whose permeability ($k_A$) and porosity ($\phi_A$) are known. Also known, is the surface tension ($\gamma_A$) of the test fluid. The saturated medium is then subjected to a drainage test, preferably centrifugation, to determine the threshold pressure ($P_A$). The contact angle is related to the known parameters via:

$$P_A = 3.264\gamma_A\cos\theta_A\sqrt{\frac{\phi_A^3}{k_A}} \quad \text{Eqn. (20)}$$

For the purpose of obtaining a cleanup ratio, however, we only need the measured threshold pressure $P_A$.

$$P_A = \frac{2\gamma_a\cos\theta_A}{r_L} \quad \text{Eqn. (21)}$$

We now introduce a theoretical maximum threshold pressure $P_{B_0}$, which is the threshold pressure that would result from a test using an identical porous material as was used to determine $P_A$, but if the base fluid without additive A exhibited a surface tension of $\gamma_B$ and the fluid were perfectly wetting. Therefore, $$P_{B_0} = \frac{2\gamma_B\cos(0)}{r_L} \quad \text{Eqn. (22)}$$

$P_{B_0}$ is the threshold pressure that would result if the base fluid without additive A were perfectly wetting. The cleanup ratio R is introduced as the ratio of the measured threshold pressure to the maximum threshold pressure.

$$R = \frac{P_A}{P_{B_0}} \quad \text{Eqn. (23)}$$

Substituting Eqn. 21 and Eqn. 22 into Eqn. 23 yields:

$$R = \frac{\gamma_A}{\gamma_B}\cos\theta_A \quad \text{Eqn. (24)}$$

Substituting Eqns. 17 and 19 for $\cos\theta_A$ yields:

$$R = \frac{\gamma_A}{\gamma_B}\frac{\sqrt{P_A P_{irr} k_A}}{3.264\gamma_A\sqrt{\phi_A^3}} = \frac{\sqrt{P_A P_{irr} k_A}}{3.264\gamma_B\sqrt{\phi_A^3}} \quad \text{Eqn. (25)}$$

Eqn. 25 can be used to evaluate the effect of an additive on cleanup. This provides a significantly superior alternative to the known Capillary Suction Time (CST) test which is the de facto standard.

In order to assess the error associated with the cleanup ratio, we simply use Eqn. 24 to show:

$$dR = \left|\frac{\cos\theta_A}{\gamma_B}\right|d\gamma_A + \left|-\frac{\gamma_A\cos\theta_A}{\gamma_B^2}\right|d\gamma_B + \left|-\frac{\gamma_A\sin\theta_A}{\gamma_B}\right|d\theta_A \quad \text{Eqn. (26)}$$

As the receding contact angle approaches zero, the error, $d\theta_A$, associated with the method used to estimate contact angle is significant, but when the contact angle is 0, the third term vanishes, making the overall error quite small, since the surface tension values are known with very good accuracy.

Testing performed on rock material particles provides good results. We have established that rock samples formed with 140- to 200-mesh particles provide reproducible results.

Description of the Drainage Cell:

A known in the art test cell can be used to perform the drainage test. Advantageously, the tube material of the cell may comprise borosilicate glass, present low expansion, a diameter of approximately 12 mm±0.2 mm and wall thickness of approximately 1 mm±0.04 mm. A frit is attached to retain the fine, loose sample material. Advantageously, the frit comprises borosilicate glass, has low expansion; has a diameter of 10 mm OD; a thickness of 2.5-2.6 mm; and the pore size is approximately 40-60 micron. The top of the cell may have a thread assembly for attaching to a permeameter. For example the thread size can be: Ace #11, ⅝" OD, 7 threads per inch, root diameter of 0.541".

Preparation of the Sample:

Generally in hydrocarbon recovery from subterranean formations, sample material from a reservoir formation is scarce. Therefore, analysis techniques that make use of only small samples is advantageous. According to some embodiments, sample sizes on the order of 5 g or less have been found to be sufficient. According to some embodiments, a measurement is made using disaggregated material, and it is understood that grinding of the sample exposes sufficient fresh surface area so as to ensuring that the test fluid is exposed to a surface very representative of that found in the undisturbed reservoir.

The use of disaggregated material is not new and the method is known to be used to evaluate the properties of extremely low permeability materials. For example, see: Schettler, P. D., Parmely, C. R., Lee, W. J., "Gas Storage and Transport in Devonian Shales" SPE Formation Evaluation, September 1989; Schettler, P. D., Parmely, C. R., "Contributions to Total Storage Capacity in Devonian Shales", SPE 23422 (1991); and Luffel, D. L., Hopkins, C. W., Schettler, P. D., "Matrix Permeability of Gas Productive Shales", SPE 26633 (1993).

Properties that can be measured using disaggregated material include permeability, porosity, and adsorption characteristics. As an example, disaggregation provides a way to determine the matrix permeability of highly fractured samples. Shales often exhibit natural fractures—even on the scale of laboratory samples. It has been found that the use of disaggregated materials provides a logical means to isolate the matrix permeability.

It is believed that the grinding of the core has minimal impact on the surface properties of the material. While the process of grinding alters the reservoir material physically, the fresh surfaces that result from grinding are believed to be quite representative of the chemical nature of the surfaces of the fractured formation in its natural state. Furthermore, the surfaces of samples shaped by drilling or sawing using either oil or water lubricants do not accurately reflect in-situ properties.

In a preferred example of the method of the invention, a sample is ground using a mixer/mill. The resulting material is dry sieved and the approximately 140/200 mesh size material fraction is retained for the measurement. This mesh size gives a fine powder. It should be noted, however, that this sieved material can contain aggregates of fines. The sample is then dried to constant weight; ideally the drying temperature will not exceed the static temperature of the underground formation that the sample is coming from.

A fixed amount of the disaggregated, sieved and dried material are weighed and transferred to a sample tube which has a frit at the bottom end. The sample is then compacted by, for example, tapping the tube on the work bench until a constant column height is achieved. Once constant height has been achieved, the sample is transferred to a centrifuge and can be subjected to the fastest spinning rate (for example at approximately 5000 rpm) for about ten minutes, which enhance mechanical stability of the material.

Measuring the Permeability of the Sample:

The gas permeability (k) of the sample rock material (in the present example, packed disaggregated material) is measured with a permeameter set-up with nitrogen using at least three different pressures. For example, the gas permeameter consists of a mass flow meter, a mass flow controller and a pressure gauge enabling the measurement of low differential pressures (for example, $\Delta p = 1-4$ psi) of a nitrogen flow (for example, $q = 0.6 - 3^{cc}/_{min}$) through the sample rock material. Given the low test pressures, the appropriate form of Darcy's Law is used to compute the permeability. Klinkenberg effects were shown to be negligible due to the relatively high permeability of a typical sample—such would not be the case were ultra-low permeability rock sample plugs used.

Determining the Porosity of the Sample:

The bulk volume of the disaggregated rock sample after tapping and centrifugation is simply determined once the length and diameter of the sample are known. The absolute volume of the sample material is determined by dividing the mass of the sample material by the grain density of the sample material as determined using a pycnometer. The porosity of the sample is finally determined by dividing the difference between the bulk volume and the absolute volume by the bulk volume.

Performing the Drainage Test:

The drainage test is preferably performed after an imbibition test with a fully saturated sample (as described, for example in U.S. patent application Ser. No. 12/914,463, entitled "Enhancing Hydrocarbon Recovery"). To conduct the imbibition step, the filled sample tube is lowered into a reservoir of imbibant until the frit is completely immersed into the test liquid. When the fluid level in the column reaches the top of the sample the imbibition is complete. The weights of the sample tube and the sample material before and after imbibition are recorded. The mass change is equal to the total mass of the imbibed fluid.

The test cell with the saturated sample is then placed into a specially constructed centrifuge adaptor. The adaptor contains a small glass vial at the bottom that receives the drained fluid. The level of the drained fluid is lower than the frit of the sample tube, so that the drained liquid cannot be re-imbibed after slowing or stopping the rotation.

After a sample has been saturated by imbibition, the sample is spun at a given speed, for example starting at 300 rpm and increasing in 100 rpm steps until 2000 rpm. Above 2000 rpm the angular speed might be increased in 500 rpm steps up to 5000 rpm. Advantageously, the respective speed is held for at least ten minutes to ensure that equilibrium between centrifugal force and capillary pressure is reached and no more fluid is driven out of the sample.

The fluid that is driven out of the sample tube is collected in a receptacle below the tube so that it does not contact the bottom end of the shale sample and, therefore, cannot be imbibed back into the sample once the centrifuge is stopped.

The amount of fluid collected in the receptacle serves as a confirmation of the amount of fluid drained. The effluent can be used for further analysis, e.g. additive retention studies.

After stopping the centrifuge, the mass of the sample tube is recorded and the tube reinserted into the centrifuge sample holder and the process repeated for the next rotational speed step. Redistribution of fluid during the slowdown of the rotor and the weighing process is so slow that it will not change the saturation profile appreciably, but care should be taken to complete these steps as quickly as possible. The rotational speed which can be achieved with the used centrifuge is about 5000 rpm. With this speed, centrifugal pressures of about 160 psi can be applied to the sample.

When the last data point at 5000 RPM is collected, the average water saturation for the respective rotational speed and the corresponding capillary pressure (=centrifugal pressure) are calculated. In another embodiment, the method described here might also be implemented on core plugs. Special adapters for core plugs have been designed and these are also fitted with a receptacle to collect the effluent.

Results

In one implementation of a method of the invention, the rock samples were shale samples from three different formations—α, β and γ. These samples were saturated with fluids containing various additives. An advancing contact angle $\Theta_a$ was determined. The fully saturated samples were placed in the centrifuge and spun out. Receding contact angles $\Theta_r$ were calculated as detailed above from the resulting data. The comparison of the measured advancing ($\Theta_a$) and receding ($\Theta_r$) contact angles is shown in Table 1 below.

| Formation | Fluid | Experimental Contact Angle | | |
|---|---|---|---|---|
| | | $\Theta_a$ [°] | $\Theta_r$ [°] | $\Delta\Theta$ [°] |
| α | KCl | 77 ± 5 | 58 ± 7 | −19 |
| | A | 55 ± 14 | 0 ± 0 | −55 |
| | B | 58 ± 13 | 27 ± 19 | −31 |
| | C | 52 ± 16 | 0 ± 0 | −52 |
| | D | 48 ± 18 | 0 ± 0 | −48 |
| | E | 52 ± 16 | 0 ± 0 | −52 |
| β | KCl | 81 ± 3 | 46 ± 12 | −35 |
| | A | 65 ± 8 | 4 ± 164 | −60 |
| | B | 72 ± 6 | 0 ± 0 | −72 |
| | C | 66 ± 7 | 0 ± 0 | −66 |
| | D | 66 ± 8 | 0 ± 0 | −66 |
| | E | 67 ± 7 | 0 ± 0 | −67 |
| γ | KCl | 81 ± 3 | 61 ± 1 | −19 |
| | A | 64 ± 9 | 56 ± 2 | −8 |
| | B | 68 ± 7 | 20 ± 4 | −48 |
| | C | 66 ± 8 | 33 ± 4 | −33 |
| | D | 64 ± 8 | 38 ± 3 | −26 |
| | E | 59 ± 11 | 55 ± 2 | −5 |

In all cases the receding contact angle is smaller than the advancing contact angle, as expected. The difference between the two dynamic contact angles ranges between 5° and 72°. In all the tests the advancing contact angles for the surfactant solutions were smaller than for the brine due to the decrease in surface tension of the respective liquids compared to brine.

When testing clearly hydrophobic rock samples (rocks from α and β) the surfactants changed the surface properties of the shale and receding contact angles of zero can be measured in most of the tests. However, in rock sample of mixed wettability (γ sample), the surfactants have a mixed impact on the surface characteristics.

Evaluating the Effect of Additives

As previously detailed above, one embodiment of the method of the invention provides a means to determine the receding contact angle and with that, the wetting characteristic of rock samples. It can also be used to compare the effect of additives on the rock itself. The clean-up ratio provides a comparison between various additives with respect to their performance on a specific rock material. The clean-up ratio, therefore, provides a means with which to optimize the design of treatments.

Figure 4:
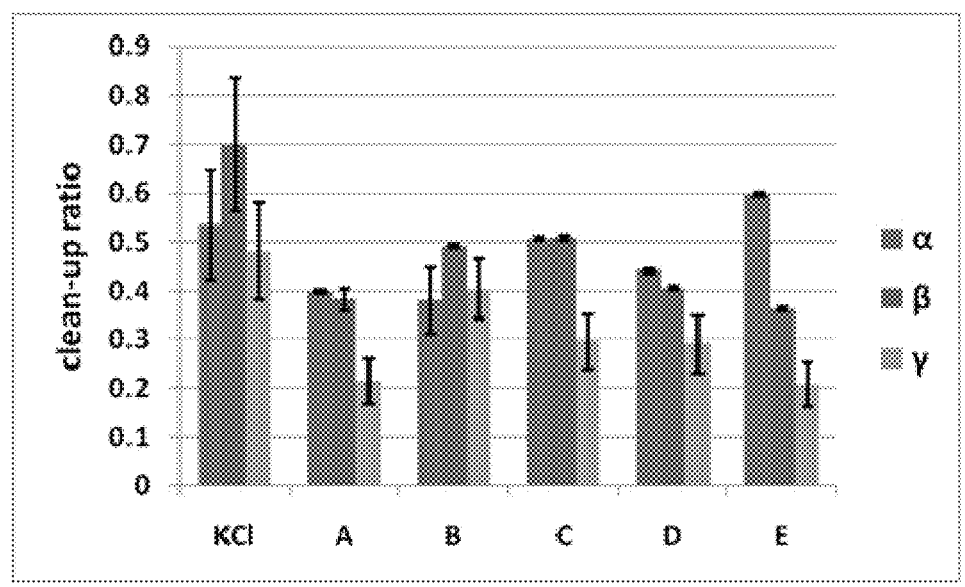
FIG. 4 represents an illustration of the use of the clean-up ratio.

FIG. 4 shows a comparison of clean-up ratios determined using five surfactant solutions and a brine solution and three formation samples. For the γ sample all the surfactants lower the clean-up ratio compared to a brine. However, surfactants E and A are markedly "better", meaning these additives displayed a lower clean-up ratio, compared to current surfactants B, C and D. This shows that improvements over current products are possible. The results for the reservoirs α and β show a different picture. Not all the surfactants decrease the clean ratio compared to a brine and it becomes important to choose the right surfactant for the job. In some cases the surfactants have too little impact on the threshold pressure to justify their cost. It is clear that surfactants react differently with various rocks. Additive E, for example, shows huge performance differences between the three formations.

When the saturation and drainage measurement is performed with a series of imbibant mixtures (e.g. water/methanol mixtures with varying mixing ratios) that have different surface tensions, a plot of a measured surface property, e.g. saturation, wetted surface area, surface energy etc, vs. surface tension can be composed. The resulting curve will have a characteristic shape depending on the wettability of the sample. A comparison with a set of curves determined for material with known wettability allows a qualitative deduction of the wettability of the measured material.

Additive and Fluid Evaluation

In addition to a need for determining the contact angle of the native rock with a brine, pure water or other simple fluid, the industry needs quantitative test methods for determining how various chemical additives to a treatment fluid can change the wetting characteristics, or capillary pressures within a subterranean rock. To address this need the method proposes embodiments to test how surface active agents (surfactants, water soluble polymers and clay stabilizers) can change the wetting condition on the surface of the rock while other physical/chemical processes are taking place in these complex rocks. Fluid and additives can do things other than modify the drainage contact angle. Additives can impact the magnitude of clay swelling in the rock, chemical weathering of the rock, and modify the native salt environment in the rock. All of these issues can lead to erroneous results and interpretations if not addressed or by applying the drainage analysis without thought. One embodiment of the method of the invention is designed so that each of these factors could be dealt with in turn, which leads to a number of examples highlighted below.

Native shales and mudstones often contain swelling clays (smectite and montmorillonite being examples), and as such the texture, three-dimensional structure and pore network of these rocks can be changed by exposure to fluids (particularly water). Also these rocks can be cemented together by soluble or partially soluble cementation agents (calcium carbonate, gypsum being examples). These changes to the rock and pore structure occur independently of the wetting behavior of the advancing fluid. This is true both for porous rock, and for granulated samples made of these rocks. This effect can complicate the interpretation of centrifuge-drainage experiments because these experiments assume that the pore structure stays constant for the duration of the experiment.

One embodiment of our invention uses knowledge of the rock, and the selective use of clay stabilizing ions to minimize this complication. Since surface tension γ is measured independently before the test, we can factor out the impact of the clay stabilizer on our calculated value for θ. Since k, and φ are independently measured for each test prior to the experiment, and since we can measure k after the experiment as well—we can detect structural changes to the matrix.

Another embodiment includes pretreatment of the surfaces of granular material to assist in the differentiation of wetting affects (on the surface of the rock) and the reduction in interfacial fluid tension (between the two mobile phases). That is so that we can distinguish between θ and γ in equation 4.

Pre-treatment of the sample can also be used to minimize the development of concentration gradients of surface active species in the rock sample. Additives that are highly adsorption prone will likely not move at the same velocity through the sample as the wetting fluid. It is also possible to analyze the effluent by taking samples after each stage of the drainage test.

In addition to changing the contact angle of surfaces we know that various additives such as polyacrylamides or polysulphonates can significantly change the permeability and porosity of samples of material due to their ability to instigate agglomeration or dispersion of fine particulate material. As such, the "comparative Washburn" method described above would not work. The proposed method of independently measuring permeability k and porosity $\phi$ is preferable in order to make the pre-treatment embodiment work and to distinguish wetting effects from other effects.

In the drainage method described in this memo, the sample of granular material is prepared as described above. The permeability k and porosity $\phi$ of the sample is then measured. The permeability is measured with respect to a non-wetting gas. The test fluid is then imbibed into the sample. This method alone could leave significant concentration gradients in the sample—especially of surface active species such as polyacrylamides. Therefore, in one embodiment of the invention, ample volume of test fluid (containing the surface active species) is placed on the top of the already saturated rock sample. This fluid is then centrifuged through the sample—treating the surface of the grains prior to the actual drainage experiment. Furthermore, the permeability of the sample to the wetting fluid can be measured during this stage as well.

Another embodiment of this method is that the test fluid and granular rock material could be slurried, and placed into the test cell as a slurry. The sample could then be centrifuged to remove excess fluid. Additional fluid could then be added to the top of the sample and a wetting-fluid saturated permeability test could be run to determine k.

Numerous shale and mudstone formations contain liquid hydrocarbons as well as gas. The imbibition test can be run against a constant or variable head.

Another embodiment comprises the determination of the contact angle with respect to a fluid which has a salt concentration(s) that mimics the connate water (or of the connate water diluted by treatment fluid) of the formation.

Advantage of the method of the invention is also that it is designed to be pragmatic—for high-throughput, rapid, atmospheric pressure testing of fluids/rocks.

While the invention is described through the above exemplary embodiments, it will be understood by those of ordinary skill in the art that modification to and variation of the illustrated embodiments may be made without departing from the inventive concepts herein disclosed. Moreover, while the preferred embodiments are described in connection with various illustrative structures, one skilled in the art will recognize that the system may be embodied using a variety of specific structures. Accordingly, the invention should not be viewed as limited except by the scope and spirit of the appended claims.

What is claimed is:

1. A method for determining a characteristic of an underground formation with a fluid comprising: measuring a permeability of a sample material of the underground formation; measuring a porosity of the sample material; performing a drainage test on the sample material using the fluid; estimating, via a processor, a geometric mean capillary pressure of the sample material from the drainage test; and determining, via the processor, a receding contact angle of the fluid on the sample material from the estimated geometric mean capillary pressure, the measured permeability, and the measured porosity; wherein estimating the geometric mean capillary pressure comprises: determining a threshold pressure representing a pressure threshold for directing a non-wetting fluid into a largest radii capillary of the sample material; determining an irreducible saturation pressure representing a pressure for directing the non-wetting fluid into a smallest radii capillary of the sample material; and calculating the geometric mean capillary pressure based on the threshold pressure and the irreducible saturation pressure.

2. The method of claim 1, further comprising disaggregating the sample material to form disaggregated sample material, wherein performing the drainage test comprises testing the disaggregated sample material.

3. The method of claim 2, wherein the disaggregation includes a grinding process.

4. The method of claim 2, wherein the disaggregated sample material is sieved to a specific size range.

5. The method of claim 1, wherein the sample material is a rock core from the underground formation.

6. The method of claim 1, further comprising performing an imbibition test on the sample material prior to the drainage test.

7. The method of claim 6, wherein the imbibition test includes an estimation of an advancing contact angle on the sample material.

8. The method of according to claim 1, wherein clay-swelling or other ancillary rock-fluid reactions of the sample material are controlled while performing the drainage test.

9. The method of according to claim 1, wherein the underground formation is a low-permeability formation with a reservoir matrix permeability of less than 0.1 mD.

10. The method of claim 1, wherein the underground formation is a low-permeability formation having a reservoir matrix permeability of less than 1 micro Darcy.

11. The method of claim 1 wherein the underground formation is a low-permeability formation penetrated by a wellbore.

12. The method of claim 1, wherein the wettability of the sample material is deduced from the receding contact angle of the fluid on the sample material.

13. The method of claim 1, wherein measuring the permeability comprising directing an inert gas through the sample material at different pressures.

14. The method of claim 1, wherein measuring the porosity comprises determining a bulk volume and an absolute volume of the sample material.

15. The method of claim 1, wherein measuring the porosity comprises determining a grain density of the sample material.

16. The method of claim 1, comprising performing an imbibition test to saturate the sample material, wherein performing the drainage test comprises spinning the saturated sample material in a centrifuge.

17. The method of claim 1, wherein performing the drainage test comprises spinning the sample material in centrifuge at a plurality of rotational speeds and determining a saturation for each of the plurality of rotational speeds.

18. The method of claim 1, wherein performing the drainage test comprises determining a saturation value for each of a plurality of capillary pressures.

19. The method of claim 1, wherein determining the threshold pressure comprises determining an inflection point of a function fit to the plurality of capillary pressures and corresponding saturation values.

20. The method of claim 1, wherein determining an irreducible saturation pressure comprises measuring an irreducible saturation of sample material and identifying a corresponding pressure as the irreducible saturation pressure.

21. The method of claim 1, wherein the geometric mean capillary pressure comprises a square root of a value representing a largest threshold pressure multiplied by a smallest threshold pressure for directing a non-wetting fluid into the sample material.

22. The method of claim 1, wherein the receding contact angle is determined based on a surface tension of the fluid.

23. The method of claim 1, wherein the receding contact angle is calculated using a following equation:

$$\cos\theta_A = \frac{P_{pro}\sqrt{k_A}}{3.264\gamma\sqrt{\phi_A^3}}$$

where $\theta$ represents the receding contact angle; $P_{pro}$ represents the estimated geometric mean capillary pressure; $k_A$ represents the measured permeability; $\phi_A$ represents the measured porosity; and $\gamma$ represents a surface tension.

24. The method of claim 1, comprising treating the underground formation with the fluid.

* * * * *